United States Patent [19]

Mathews et al.

[11] Patent Number: 4,816,246
[45] Date of Patent: Mar. 28, 1989

[54] PERMANENT WAVE COMPOSITION

[75] Inventors: Roger A. Mathews, Newbury Park; Edward R. Moore, Canoga Park; David W. Cannell, Los Angeles, all of Calif.

[73] Assignee: Redken Laboratories, Inc., Canoga Park, Calif.

[21] Appl. No.: 30,738

[22] Filed: Mar. 25, 1987

[51] Int. Cl.$^4$ .............................................. A61K 7/09
[52] U.S. Cl. ........................................................ 424/72
[58] Field of Search ................................... 424/72, 71

[56] References Cited

U.S. PATENT DOCUMENTS

| | | | |
|---|---|---|---|
| 2,719,815 | 10/1955 | Sanders | 424/72 |
| 3,880,174 | 4/1975 | Wajaroff | 132/7 |
| 3,975,515 | 8/1976 | Wajaroff et al. | 424/72 |
| 4,134,411 | 1/1979 | Yamazaki | 132/7 |
| 4,158,704 | 6/1979 | Baer et al. | 424/72 |
| 4,192,863 | 3/1980 | Kondo | 424/72 |
| 4,273,143 | 6/1981 | Klemm et al. | 132/7 |
| 4,301,820 | 11/1981 | Cannell et al. | 132/7 |
| 4,313,933 | 2/1982 | Yamazaki | 424/72 |
| 4,424,820 | 1/1984 | Cannell et al. | 132/7 |
| 4,459,284 | 7/1984 | Azuma et al. | 424/72 |
| 4,504,466 | 3/1985 | Eda . | |
| 4,532,950 | 8/1985 | Lang et al. | 132/7 |
| 4,547,368 | 10/1985 | Kubo et al. | 424/72 X |
| 4,548,811 | 10/1985 | Kubo et al. | 424/72 X |
| 4,600,028 | 7/1986 | Edman et al. | 132/7 |

Primary Examiner—George F. Lesmes
Assistant Examiner—Susan S. Rucker
Attorney, Agent, or Firm—Christie, Parker & Hale

[57] ABSTRACT

This hair waving composition has a self-limiting reaction so that reduction of sulfhydryl bonds and reduction of cystine is effectively discontinued after an interval, for minimizing potential for damage to hair when making a permanent wave. The self-limiting effect is obtained by using a composition containing both the ammonium and monoethanolamine salts of a suitable mercaptan, preferably thioglycolic acid. In a composition having a pH in the range of 9 to 9.5 the ratio of ammonium thioglycolate to monoethanolamine thioglycolate is in the range of from 2:1 to 8:1. Preferably the total concentration of ammonium thioglycolate plus monoethanolamine thioglycolate is in the of from 3% to 12% by weight. Such a composition may also include from 1% to 10% by weight surfactant, up to 1.5% by weight sequestrant for metal ions, and conditioners, colors, fragrances and the like.

32 Claims, 1 Drawing Sheet

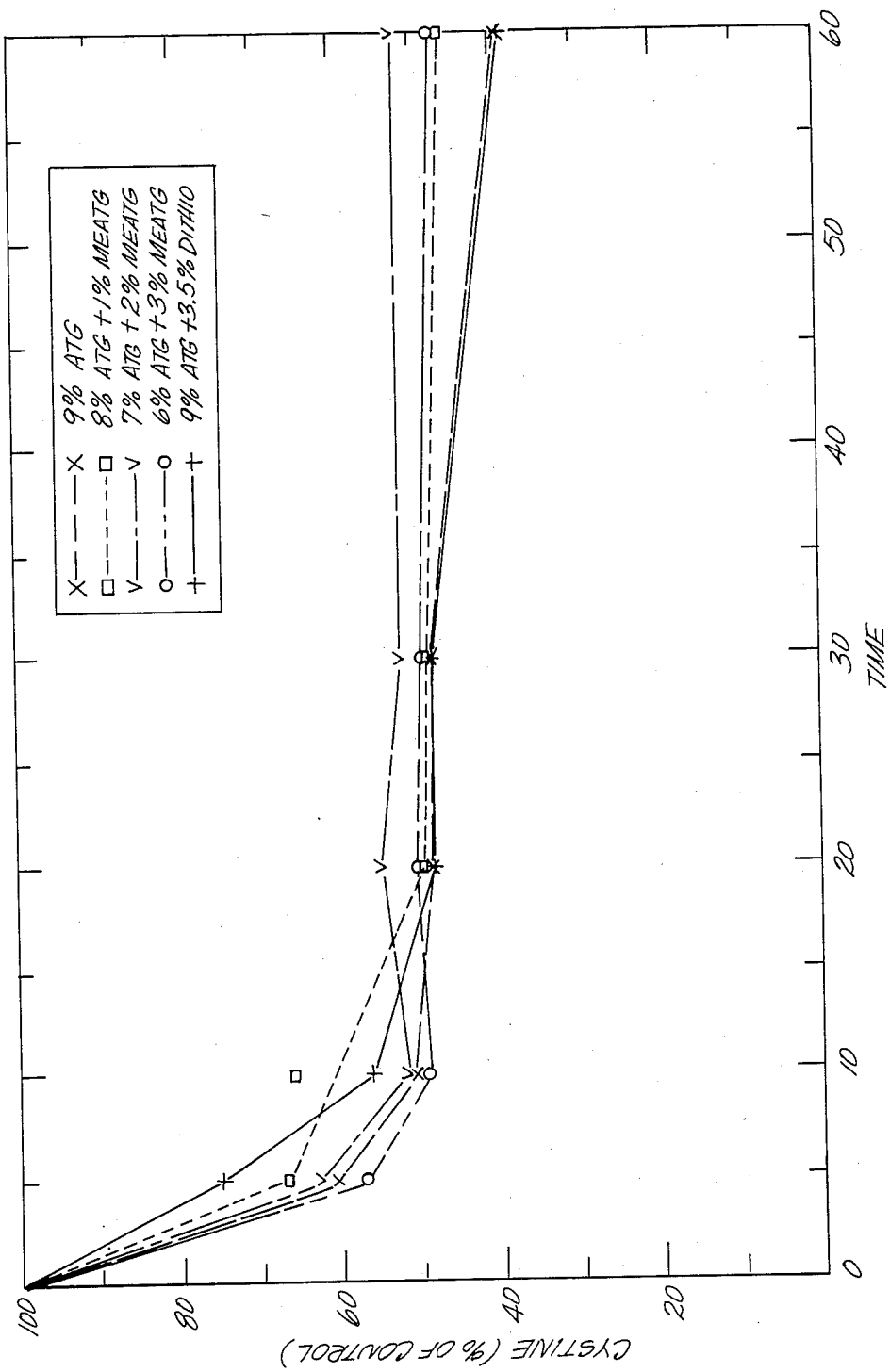

PERMANENT WAVE COMPOSITION

BACKGROUND OF THE INVENTION

This invention concerns a hair treatment composition which is self-limiting in that it cleaves disulfide bonds of keratin to an extent sufficient to impart a desirable ability to set a wave in the hair, then limits further reaction which may degrade the hair.

When a waving lotion is applied to hair, the following chemical reactions may occur:

$$K_1SSK_2 + RSH \rightarrow K_1SSR + K_2SH \qquad \text{I.}$$

$$K_1SSR + R'SH \rightarrow K_1SH + RSSR' \qquad \text{II.}$$

As used in these equations, KSSK represents two keratin protein chains (K) joined by a cystine disulfide (SS) bond, and RSH represents a salt of thioglycolic acid. The usual salts are ammonium thioglycolate (ATG) or monoethanolamine thioglycolate (MEATG) as the waving agent. In these equations, KSSR represents a "mixed disulfide" of one keratin protein chain and the waving agent, and the KSH represents a reduced keratin protein chain liberated from its adjacent protein counterpart by the reaction of the waving agent.

It appears that almost irrespective of the pH and the waving agent (ATG or MEATG) used, the first reaction proceeds readily. That is, the initial cleavage of the interprotein disulfide bond and formation of an asymmetrical mixed disulfide occurs at approximately the same rate and to the same extent at pH7.0 as at pH9.2.

In sharp contrast to the relatively facile completion of the first reaction, the cleavage of the mixed disulfide ($K_1SSR$) by a second molecule of reducing agent (R'SH) in the second reaction proceeds with more difficulty. The second reaction appears to be much more pH dependent than the first reaction; increasing pH stimulates the second reaction.

These reactions comprise a two-step mechanism in the chemical reduction of hair for a time sufficient to impart the required degree of softening of the fibers so that a wave can be formed. The wave can then be set by reversing the reactions with an oxidant such as hydrogen peroxide or sodium bromate.

The time of processing required to impart a cosmetically acceptable wave has been judged in any of several ways. With many waving systems the "test curl" method is practiced. This can require appreciable skill on the part of the operator. Alternatively, processing may be for a predetermined time, as specified by the instructions from the manufacturer. This timing method attempts to average hair type and other conditions of application so that the wave is effective on most heads in the specified time without causing excess hair damage due to over processing. Again, to achieve desired results with a broad variety of hair types may require a skilled operator.

For such reasons it has been considered desirable to formulate a self-limiting waving system which cleaves keratin disulfides in the first reaction to an extent sufficient to impart a desirable wave, and then effectively limit further reaction which is degrading to the fiber.

Several techniques have been proposed for self-limiting waving reactions. One concept is to rely on mass action to inhibit the two-step reaction from proceeding toward completion. By including a product of the second reaction (RSSR) in the waving solution, it is believed that the position of the equilibrium will not proceed too far toward cleavage and gradual fiber destruction. Such a technique is described in U.S. Pat. No. 4,273,143 by Klemm et al. Such a composition may include the "dithio" form (RSSR) of the waving agent in the waving solution. Such a solution may contain a diammoniumdithiodiglycolic acid salt or a diammonium-diglyceryldithioglycolate.

In reality, true equilibrium is not obtained in the time frame of a salon permanent wave and the dithio form of the waving agent does not appear to limit the reaction. Compositions relying solely on the mass action effect may continue to react with the mixed disulfide with concomitant increasing destruction of the treated hair.

Another means of limiting the action of waving solutions is disclosed in U.S. Pat. No. 4,532,950 by Lang et al. In this technique, just before use, a composition containing the reducing agent (RSH) is mixed with a second composition containing unsaturated aliphatic compounds. The activity of the reducing agent is decreased by gradual adduction of the reducing agent to the unsaturated carbon-carbon bond. This is probably not much different from starting with a lower initial concentration of the waving agent.

It is desirable to provide a different technique for self-limiting the reaction of a waving composition with hair. Such self-limiting action minimizes the potential for hair damage due to over processing. It is desirable that the composition be no more expensive than present compositions and not require special skills on the part of the operator.

SUMMARY OF THE INVENTION

There is, therefore, provided in practice of this invention according to a presently preferred embodiment, a water base hair waving composition comprising ammonium thioglycolate plus monoethanolamine thioglycolate in the range of from 3 to 12 percent by weight, where the ratio of ammonium thioglycolate to monoethanolamine thioglycolate is in the range of from 2:1 to 8:1 and the pH is in the range of from 9 to 9.5. Other compositions containing ammonium thioglycolate plus monoethanolamine thioglycolate may also be used in practice of this invention. For example, when the pH is in the range of from 6.8 to 7.2, the ratio of ammonium thioglycolate to monoethanolamine thioglycolate is in the range of from 1:8 to 1:2.

BRIEF DESCRIPTION OF THE DRAWINGS

These and other features and advantages of the present invention will be appreciated as the same becomes better understood from the following detailed description when considered in connection with the accompanying drawing which comprises a graph of the proportion of cystine bonds in hair as a function of time for various permanent wave compositions.

DETAILED DESCRIPTION

It has been appreciated that the nature of the alkaline moiety of the reducing agent (RSH) affects the rate of waving. For example, when an alkaline permanent waving solution is used, ammonium thioglycolate (ATG) is more effective than monoethanolamine thioglycolate (MEATG). When the pH is 7, this situation is reversed and the MEATG is more effective than ATG. It has now been found that MEATG has appreciably higher activity in the second of the reactions described above than in the first reaction. ATG has greater activity in the first keratin cleavage reaction. That is, ATG favors the initial cleavage to form a mixed disulfide over the second reaction which forms a dithiodiglycolate. Contrariwise, MEATG favors the second reaction over the first.

A truly synergistic effect can be noted with certain proportions of admixtures of ATG and MEATG. For example, at a pH of 9.2 a mixture of 7% ATG and 2% MEATG (by weight) gave a curl efficiency of 72%, while 9% ATG alone gave an efficiency of 67% under otherwise identical conditions. A mixture of 3% MEATG and 6% ATG had a curl efficiency of 67%.

Further, it was discovered with certain mixtures of ATG and MEATG that after 20 to 30 minutes of processing, the waving efficiency did not continue to increase with time up to an hour. This effect is noted only within a narrow range of proportions of the two components. Compositions containing mixtures outside of the preferred range appear to continually process hair.

Preferably, the pH of the permanent wave solution is in the range of from 9 to 9.5. In this range the composition contains ATG and MEATG in a ratio of from 2:1 to 8:1. A total concentration of ATG plus MEATG of 9% by weight is preferred for curling normal hair. Solutions of lower strength, down to 3% by weight, are suitable for fragile, chemically pre-treated hair. Solutions having a strength up to 12% by weight total MEATG and ATG may be employed for hair exceptionally resistent to permanent waving.

In a preferred composition, the ammonium salt, ATG, comprises from 6% to 8% of the total and the monoethanolamine salt, MEATG, comprises from 1% to 3% of the total. Thus, for example, at one end of the range the solution comprises 3% MEATG and 6% ATG, and at the other end of the range, comprises 1% MEATG and 8% ATG.

A particularly preferred composition has 9% by weight total ATG plus MEATG in the proportion of 3.5:1 ATG to MEATG, that is, 7% ATG and 2% MEATG.

While not being bound by theory, it is believed that compositions provided in practice of this invention exert their self-limiting effect at the level of the second reaction in the waving process. That is, cleavage of the mixed disulfide of keratin bound cysteine and the thioglycolate waving agent.

Since ATG apparently has a greater affinity for cleavage of interprotein disulfides (KSSK) while MEATG exhibits a greater affinity for cleavage of the mixed disulfides (KSSR) the postulated reactions effecting self-limitation are believed to be as follows:

KSSK+(NH₄)RSH→KSSR(NH₄)+KSH     I.

KSSR(NH₄)+(MEA)RSH→KSH+(NH₄)RSSR-(MEA)     II.

As the concentration of (MEA)RSH declines via preferential cleavage of KSSR(NH₄) and subsequent entry into the "mixed salt" form of dithiodiglycolate (NH₄)RSSR(MEA), the rate of cleavage of KSSR(NH₄) declines, thereby tending to limit the process to the first-stage reaction. Therefore, as the concentration of the component [(MEA)RSH] limiting the reaction declines, the mixed disulfide [KSSR(NH₄)] cannot be as readily cleaved. As a consequence of this, the reaction tends to limit its own progress.

When the solution is alkaline with a pH in the range of from 9 to 9.5 this effect is observed only when the proportions of ATG and MEATG fall within the preferred ranges described above.

When the pH of the solution is about 7 an effective composition containing both ATG and MEATG has different proportions than when the solution is alkaline. The total concentration of ATG plus MEATG should be in the range of from 3% to 12% by weight and is preferably 9% by weight. Surprisingly, the ratios of ATG and MEATG are just the reverse of the alkaline composition. Thus the ratio of ATG to MEATG is in the range of from 1:2 to 1:8. It is preferred that the ratio of ATG to MEATG be 1:3.5. It is also preferred that the total concentration of ATG plus MEATG be 9% by weight although the total concentration may be as low as 3% for a fragile hair and as high as 12% by weight for resistent hair.

Additional materials are included in a hair waving composition formulated according to principles of this invention. These include, for example, surfactant, a metal sequestering agent, ammonium hydroxide or organic bases to adjust pH, fragrance, conditioners, thickeners, colors and other additives well known in the art.

Preferably, the composition includes surfactants that are either non-ionic, cationic or anionic, or a mixture thereof, in the range of from 1% to 10% by weight of the solution. Preferably, the surfactant is nonionic and present in a proportion of about 6% by weight. The surfactant or surfactants selected should result in a hydrophobic/lipophilic balance (HLB) of from 14.5 to 17.0 and preferably with an HLB of 16.9. Examples of suitable non-ionic surfactants are Ameroxal OE-20, a polyethyleneglycol ether of oleyl alcohol, and Brij 35, a polyethyleneglycol ether of lauryl alcohol, available from ICI United States, Inc., Wilmington, Del.

Ethylenediaminetetraacetic acid (EDTA) derivatives thereof, such as HEDTA, are preferred chelating agents for sequestering iron and other metal ions. Preferably EDTA is present in the range of from 0.1% to 1.5% by weight.

To make an alkaline composition it is preferred to include aqua ammonia in the range of from 0.1% to 2% by weight. Preferably about 0.85% by weight aqua ammonia is employed to give a pH of 9.2. Organic bases such as monoethanolamine may also be employed, but are generally avoided because of a slippery feel imparted to hair.

The balance of the composition is water and such buffers, soaps, conditioners, thickeners, colors, fragrances and other additives as may be desired.

In addition, a composition provided in practice of this invention may include up to about 4% by weight diammoniumdithiodiglycolate. As pointed above, such a dithioglycolate may have a mass effect in reducing reaction rate. It appears however, that the effect is minimal.

A particularly preferred embodiment of the invention comprises 7.0% by weight ATG, 2.0% MEATG, an EDTA derivative such as 0.25% Versenex 120, 6.0% of an non-ionic surfactant such as Ameroxal OE-20, 0.85% aqua ammonia, and 0.25% fragrance. The balance of the composition is water.

Another alkaline composition provided in practice of this invention comprises 7% by weight ATG, 2% by weight MEATG, 1.5% by weight diammoniumdithioglycolate, 4% by weight Brij 35, 0.5% Versenex 120, 5% Urea, 0.5% of a hydrolyzed protein such as Peptein 2000, 0.25% fragrance, 1.06% aqua ammonia, and a balance of water.

Laboratory tests have substantiated the self-limiting action on human hair of compositions as provided in practice of this invention. As a permanent wave solution contacts hair, reduction of cystine linkages is initiated. Cystine is reduced to carboxymethylthiocysteine and further to cysteine. As processing continues the level of cystine decreases, therefore, the kinetics of cystine cleavage offers a sensitive biochemical measure of the progress of the reactions induced by a permanent wave composition.

In one series of tests the kinetic course of cleavage of cystine was ascertained for each of five compositions differing only in the proportions of ATG and MEATG. These compositions contained respectively 9% ATG; 8% ATG plus 1% MEATG; 7% ATG plus 2% MEATG; 6% ATG plus 3% MEATG; and 9% ATG plus 3.5% diammonium-dithioglycolate.

Replicate swatches of human hair were saturated with one of the above compositions and kept at room temperature in a plastic bag to prevent drying out. At intervals of 5, 10, 20, 30, and 60 minutes respectively, after saturation, the swatches were sampled. These samples and samples taken before saturation were analyzed for cystine by standard laboratory techniques. The drawing comprises a graph illustrating the proportion of cystine determined in each of the samples. The control at zero time and 100% comprises the sample of hair before saturation.

It can be seen from this graph that the samples containing 9% ATG, either alone or with 3.5% diammoniumdithioglycolate, continued to decrease the cystine concentration over the 60 minutes of treatment. On the other hand, compositions containing mixtures of ATG and MEATG show no further decrease in cystine content after about 20 minutes or less of contact with the hair. Thus, it can be seen that a 9% concentration of ATG continues to process and weaken hair after a typical 20 minute processing time, whereas the compositions containing a synergistic mixture of ATG and MEATG are self-limiting, and effectively discontinue processing at some time before more than 20 minutes has elapsed.

In another series of tests the tensile properties of individual hairs were compared. In these tests to accentuate the potential for damage by a permanent waving solution, the hair was pre-bleached for one hour to a pale yellow color. Such pre-bleached hair without application of any permanent waving solution served as a control. Two permanent waving solutions were compared. One of these contained 9% ATG. The other solution contained 7% ATG and 2% MEATG, as preferred in practice of this invention. The pre-bleached hair swatches were waved with either of these solutions at room temperature for 20 minutes. Hairs from each swatch were tested for structural integrity by stress-strain analysis by either a conventional Instron tensile tester or a Redken Digital Trichogram. 20 hairs of each sample were tested in the Instron machine. 81 hairs of each sample were tested in the Trichogram apparatus.

Table I indicates results of these tests. In this table composition 1 is the control swatch which was not contacted with a permanent waving solution. Composition 2 contains a conventional quantity of 9% ATG. Composition 3 contains a mixture of 7% ATG and 2% MEATG as preferred in practice of this invention.

Instron elongation refers to the total jaw separation of the machine when the hair fiber breaks, after starting with a 75 millimeter (3") gage-length. The integral of force refers to the area under the stress-strain curve as measured on the Instron machine (the units are not significant). The Trichogram elongation refers to the percentage elongation of the specimen to its breaking point. The breaking force is the number of grams required to break the hair. The values listed in Table I are an numerical average (mean) of 20 hairs in the case of the Instron tests and 81 hairs in the case of the Trichogram test.

TABLE I

| Composition | 1 | 2 | 3 |
|---|---|---|---|
| ATG | — | 9% | 7% |
| MEATG | — | 0% | 2% |
| Instron elongation | 119 mm. | 135 mm. | 121 mm. |
| Integral of force | 1212 | 963 | 1021 |
| Trichogram elongation | 35.3% | 33.3% | 34.9% |
| Break force | 75.1 gr. | 66.6 gr. | 69.4 gr. |

The absolute values of the mechanical properties of the hair in Table I are not significant. What is significant is that in all such properties, the measured values of composition 3, as provided in practice of this invention, are closer to the values for the control than are the values for composition 2 containing 9% ATG. From these values it is apparent that hair waved with a composition as provided in practice of this invention is stronger and less elastic than hair waved with a composition outside the purview of this invention.

The permanent waving efficiency of various compositions within and without the scope of this invention have also been measured. A conventional measure of permanent waving efficiency was employed. In such a test a swatch of hair is wrapped in a serpentine path on rows of pegs and treated with a permanent waving solution. After a desired period of exposure to the reducing waving solution, the hair is rinsed and set with an oxidizer in a conventional manner. The wet hair is removed from the pegs and the length of a portion of the waved swatch is compared with the length of a similar portion of the rows of pegs (e.g. five wave lengths). Efficiency is indicated as a percentage based on the increased length of the waved specimen as compared with the distance between the respective pegs. An efficiency of 100% represents hair that did not change dimension upon removal from the pegs. Generally speaking, increasing efficiency is desired up to about 85%, above which damage to the hair may occur.

Table II indicates the permanent waving efficiency for compositions within and without the scope of this invention as a function of treatment time in minutes.

TABLE II

| | Composition (percent) | | | Efficiency (%) at time | | | |
|---|---|---|---|---|---|---|---|
| No. | ATG | MEATG | dithio | 10 | 20 | 30 | 60 |
| 1 | 9 | 0 | 0 | 68 | 71 | 74 | 77 |
| 2 | 8 | 1 | 0 | 72 | 74 | 74 | 77 |
| 3 | 7 | 2 | 0 | 72 | 74 | 74 | 74 |
| 4 | 6 | 3 | 0 | 68 | 74 | 77 | 77 |
| 5 | 7 | 2 | 1.5 | 60 | 62 | 64 | 64 |
| 6 | 9 | 0 | 3.5 | 53 | 58 | 58 | 68 |

Compositions hereinabove described in detail are alkaline with the pH raised to about 9 to 9.5 by addition of ammonia, monoethanolamine or the like. A suitable permanent waving composition having essentially neutral pH can also be formulated in practice of this invention. In such an embodiment, there is no extra source of alkalinity, and pH is in the range of from 6.8 to 7.2. The concentration of ATG plus MEATG in such a composition is preferably in the range of from 6% to 12% by weight with 9% by weight being particularly preferred. Within this pH range the ratio of MEATG to ATG in the composition is in the range of from 2:1 to 8:1. It is particularly preferred that the ratio of the concentration of MEATG to ATG be 3.5 to 1. Such a composition also includes from 1% to 10% by weight of non-ionic, anionic or cationic surfactant, preferably about 6% by weight of non-ionic surfactant. The surfactants selected should have a hydrophobic/lipophilic balance of from 14.5 to 17.0 and preferably a hydrophobic/lipophilic balance of 16.9. Exemplary non-ionic surfactants are Ameroxal OE-20 and Brij 35. It also desirable that the composition include an agent for sequestering metals, such as EDTA in the range of from 0.1% to 1.5% by weight. An exemplary composition contains 0.25% by weight of EDTA or its equivalent.

In other words, a permanent waving solution having a pH in the range of from 6.8 to 7.2 has a concentration of ammonium thioglycolate in the range of from 1% to 3% and preferably 2%. It also has monoethanolamine thioglycolate in the range of from 6% to 8% and preferably 7%. If desired, such a composition may also include up to about 4% diammoniumdithiodiglycolate. Other ingredients may include conditioners, thickeners, colors, fragrances and similar additives known in the art.

Although the particularly preferred compositions comprise mixtures of the ammonium and the monoethanolamine salts of thioglycolic acid, other hair waving compositions may be formulated from water soluble, non-toxic, nonodorous ammonium and monoethanolamine salts of other mercaptans, such as salts of glycerylmonothioglycolic acid, for example. Other suitable mercaptans include thiolactic acid, thioglycerol and $\beta$-mercaptoethylamine. The total concentration of the combined ammonium and monoethanolamine salts of these mercaptans should contain from 0.33 to 1.3 milliequivalents of sulfhydryl reducing equivalents per gram of solution, preferably one milliequivalent per gram.

Such a composition having a pH from 9 to 9.5 should have a weight ratio of the ammonium salt to the monoethanolamine salt in the range of from 2:1 to 8:1. About 0.4 to 0.8 milliequivalents of alkalinity per gram of solution from aqua ammonia or monoethanolamine are included to produce the desired range of pH. As described above, such a composition may include surfactants, soaps, conditioners, combing aides, sequestrants, buffers, colors, fragrances, thickeners and similar materials known in the art.

Alternatively, such a composition may have a neutral pH in the range of from 6.8 to 7.2 without addition of extra alkali. In such a composition the ratio of the monoethanolamine form of the mercaptan to the ammonium form of the mercaptan is in the range of from 2:1 to 8:1. Preferably the ratio is about 3.5:1.

Although specific embodiments and examples have been set forth in detail herein, it will be apparent to one skilled in the art that there may be other modifications and variations of the compositions provided in practice of this invention. It is therefore to be understood that within the scope of appended claims, the invention may be practiced otherwise than as specifically described.

What is claimed is:

1. A water-based self-limiting hair waving composition comprising ammonium thioglycolate plus monoethanolamine thioglycolate in the range of from 3% to 12% by weight, the ratio of ammonium thioglycolate to monoethanolamine thioglycolate being in the range of from 2:1 to 8:1 and having a pH in the range of from 9 to 9.5.

2. A hair waving composition as recited in claim 1 further comprising surfactant in the range of from 1% to 10% by weight.

3. A hair waving composition as recited in claim 2 further comprising up to 1.5% by weight sequestrant for metal ions.

4. A hair waving composition as recited in claim 1 wherein the ratio of ammonium thioglycolate to monoethanolamine thioglycolate is 3.5:1.

5. A hair waving composition as recited in claim 1 wherein the total concentration of ammonium thioglycolate plus monoethanolamine thioglycolate is 9%.

6. A hair waving composition as recited in claim 1 further comprising up to 4% by weight diammoniumdithiodiglycolate.

7. A water-based self-limiting hair waving composition comprising ammonium thioglycolate in the range of from 6% to 8% by weight and monoethanolamine thioglycolate in the range of from 1% to 3% by weight, and having a pH in the range of from 9 to 9.5.

8. A hair waving composition as recited in claim 7 further comprising surfactant in the range of from 1% to 10% by weight.

9. A hair waving composition as recited in claim 8 further comprising up to 1.5% by weight sequestrant for metal ions.

10. A hair waving composition as recited in claim 8 comprising 7% by weight ammonium thioglycolate and 2% by weight monoethanolamine thioglycolate.

11. A hair waving composition as recited in claim 10 comprising 6% of non-ionic surfactant and up to 1.5% by weight sequestrant for metal ions.

12. A water-based self-limiting hair waving composition comprising both ammonium and monoethanolamine salts of mercaptans selected from the group consisting of thioglycolic acid, thiolactic acid, glycerylmonothioglycolic acid, thioglycerol and $\beta$-mercaptoethylamine in a concentration of from 0.33 to 1.3 milliequivalents of sulfhydryl reducing equivalents per gram of solution, the weight ratio of the ammonium salt to the monoethanolamine salt being in the range of from 2:1 to 8:1 and having a pH in the range of from 9 to 9.5.

13. A hair waving composition as recited in claim 12 further comprising surfactant in the range of from 1% to 10% by weight.

14. A hair waving composition as recited in claim 13 further comprising up to 1.5% by weight sequestrant for metal ions.

15. A water-based self-limiting hair waving composition comprising ammonium thioglycolate plus monoethanolamine thioglycolate in the range of from 3% to 12% by weight, the ratio of monoethanolamine thioglycolate to ammonium thioglycolate being in the range of from 2:1 to 8:1 and having a pH in the range of from 6.8 to 7.2.

16. A hair waving composition as recited in claim 15 further comprising surfactant in the range of from 1% to 10% by weight.

17. A hair waving composition as recited in claim 15 further comprising up to 1.5% by weight sequestrant for metal ions.

18. A hair waving composition as recited in claim 15 wherein the ratio of monoethanolamine thioglycolate to ammonium thioglycolate is 3.5:1.

19. A hair waving composition as recited in claim 15 wherein the total concentration of ammonium thioglycolate plus monoethanolamine thioglycolate is 9%.

20. A hair waving composition as recited in claim 15 further comprising up to 4% by weight diammoniumdithiodiglycolic.

21. A water-based self-limiting hair waving composition comprising monoethanolamine thioglycolate in the range of from 6% to 8% by weight and ammonium thioglycolate in the range of from 1% to 3% by weight, and having a pH in the range of from 6.8 to 7.2.

22. A hair waving composition as recited in claim 21 further comprising surfactant in the range of from 1% to 10% by weight.

23. A hair waving composition as recited in claim 22 further comprising up to 1.5% by weight sequestrant for metal ions.

24. A hair waving composition as recited in claim 22 comprising 7% by weight monoethanolamine thioglycolate and 2% by weight ammonium thioglycolate.

25. A hair waving composition as recited in claim 24 comprising 6% of non-ionic surfactant and up to 1.5% by weight sequestrant for metal ions.

26. A water-based self-limiting hair waving composition comprising both ammonium and monoethanolamine salts of mercaptans selected from the group consisting of thioglycolic acid, thiolactic acid, glycerylmonothioglycolic acid, thioglycerol and β-mercaptoethylamine in a concentration of from 0.33 to 1.3 milliequivalents of sulfhydryl reducing equivalents per gram of solution, the ratio of the monoethanolamine salt to the ammonium salt being in the range of from 2:1 to 8:1 and having a pH in the range of from 6.8 to 7.2.

27. A hair waving composition as recited in claim 26 further comprising surfactant in the range of from 1% to 10% by weight.

28. A hair waving composition as recited in claim 27 further comprising up to 1.5% by weight sequestrant for metal ions.

29. A water-based self-limiting hair waving composition comprising both ammonium thioglycolate and monoethanolamine thioglycolate in a total concentration in the range of from 3% to 12% by weight, the ratio of monoethanolamine thioglycolate to ammonium thioglycolate being in the range of from 1:8 to 8:1 and the pH being in the range of from 6.8 to 9.5.

30. A hair waving composition as recited in claim 29 comprising from 0.1% to 2% aqua ammonia.

31. A hair waving composition as recited in claim 29 further comprising surfactant in the range of from 1% to 10% by weight.

32. A hair waving composition as recited in claim 31 further comprising up to 1.5% by weight sequestrant for metal ions.

* * * * *